United States Patent
Hall et al.

[11] Patent Number: 6,071,240
[45] Date of Patent: Jun. 6, 2000

[54] METHOD AND APPARATUS FOR COHERENCE IMAGING

[75] Inventors: Anne Lindsay Hall, New Berlin, Wis.; Kai E. Thomenius, Clifton Park, N.Y.; Lewis Jones Thomas, II, Palo Alto, Calif.; Kenneth Wayne Rigby, Clifton Park, N.Y.

[73] Assignee: General Electric Company, Milwaukee, Wis.

[21] Appl. No.: 09/223,951

[22] Filed: Dec. 31, 1998

Related U.S. Application Data

[63] Continuation-in-part of application No. 08/934,692, Sep. 22, 1997, Pat. No. 5,910,115.

[51] Int. Cl.[7] .................................................. A61B 8/00
[52] U.S. Cl. .................................................. 600/443
[58] Field of Search ........................... 600/443, 447, 600/458; 73/625–626; 382/210, 216, 260

[56] References Cited

U.S. PATENT DOCUMENTS

| | | | |
|---|---|---|---|
| 5,476,098 | 12/1995 | O'Donnell | 128/661.01 |
| 5,619,998 | 4/1997 | Abdel-Malek et al. | 600/443 |
| 5,667,373 | 9/1997 | Wright et al. | 600/443 |
| 5,910,115 | 6/1999 | Rigby | 600/443 |

OTHER PUBLICATIONS

Reiter et al., "A Semblance–Guided Median Filter," Geophys. Prospect., vol. 51 (1993), pp. 15–41.
Szabo et al., "Velocity Guided Median Filtering Applications to Ultrasonic Imaging," 23rd Int'l Symp. Acoust. Imaging, Boston, MA, Apr. 13–16, 1997. Printed by Brattleboro Printing, Inc., 11 Elm St., Brattleboro, VT 05303.

*Primary Examiner*—Francis J. Jaworski
*Attorney, Agent, or Firm*—Dennis M. Flaherty; Christian G. Cabou; Phyllis Y. Price

[57] ABSTRACT

A method and an apparatus for adaptively suppressing incoherent data in a coherent imaging system. A focused ultrasound beam is transmitted with conventional transmit beamforming time delays. The returning echo signals are processed along two separate receive signal processing paths. The time delays along one processing path are set for traditional coherent receive beamforming, while the time delays along the other processing path are set to apply incoherent summing to the same set of return signals (e.g., time delays equal to zero). Then at each point in the receive beam or vector, the coherent and incoherent summation signals are compared. If the coherent and incoherent summation signals are of like amplitude, the beamformed signal of the first processing path is deemed incoherent, and its display is suppressed in the final image.

31 Claims, 5 Drawing Sheets

METHOD AND APPARATUS FOR COHERENCE IMAGING

RELATED PATENT APPLICATION

This application is a continuation-in-part application of U.S. patent application Ser. No. 08/934,692 filed on Sep. 22, 1997 and now U.S. Pat. No. 5,910,115.

FIELD OF THE INVENTION

This invention generally relates to coherent imaging methods which apply a phased array antenna. In particular, the invention relates to methods for improving medical ultrasound images by means of data-dependent filtering.

BACKGROUND OF THE INVENTION

Conventional ultrasound imaging systems comprise an array of ultrasonic transducer elements which are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair. In particular, because of the beamforming time delays applied to both the transmitted and received signals for each transducer element, backscattered signals from tissue along the line of the steering angle and at the transmit focal zone position add up coherently and produce large composite beam sums, while back-scatter from tissue off the beam axis and out of the transmit focal zone add incoherently and produce a relatively smaller beam sum.

Tissue types and anatomical features are most easily differentiated in an ultrasound image when they differ in image brightness. Image brightness on conventional medical ultrasound imaging systems is a function of the amplitude of the receive beamformed signal, i.e., after coherent summation of the delayed receive signals on each transducer element. More precisely, the logarithm of the amplitude of the beamformed signal is displayed, with user-adjustable gain and contrast, and perhaps a choice of a handful of gray-scale mapping tables.

Unfortunately, very strong signals off of the ultrasound beam steering direction can often produce a signal which, when added incoherently, still produces a large enough composite signal to degrade or mask the coherently summed smaller tissue signals. In addition, structures in the body, such as varying layers of muscle and fat, can produce ultrasound time-of-flight variations that cause tissue signals along the steered direction to add incoherently, thereby degrading the resolution in the display image of those tissue structures.

There is a need for an imaging technique that would detect when the acoustic data acquired by the imager is incoherent and then adaptively suppress that incoherent data to mitigate degradation of the displayed image.

SUMMARY OF THE INVENTION

The present invention comprises a method and an apparatus for improving medical ultrasound images by means of data-dependent filtering. The filter increases contrast between tissue types by distinguishing them on the basis of the degree of coherence of the receive ultrasound signals. The method also provides some suppression of speckle noise without significantly degrading resolution. The method can be implemented in real-time with only a modest change to the hardware of an existing ultrasound imaging system. The invention can be incorporated in the beamforming system of a digital ultrasound imaging system having either a baseband beamformer or a pure time-delay beamformer (also known as an RF beamformer).

The preferred embodiment of the invention comprises a method to adaptively recognize situations that cause incoherent image formation and the consequent image degradation. First, an ultrasound beam is transmitted along a line of sight in the traditional beamforming fashion, using the appropriate transmit beamforming time delays. The returning signals from his transmit firing are then processed along two separate receive signal processing paths. The time delays along one processing path are set for traditional coherent receive beamforming along the line of sight of the transmit beam, while the time delays along the other processing path are set to apply incoherent summing to the same set of return signals (e.g., time delays equal to zero). Then at each point in the receive beam or vector, the coherent and incoherent summation signals are compared. If these signals are very different, the beamformed signal output by the first processing path is deemed coherent and allowed to be displayed. If the coherent and incoherent summation signals are of like amplitude, that same beamformed signal is deemed incoherent, and its display is suppressed in the final image. This process is repeated for each vector of acoustic data acquired during multiple transmit firings in a scan plane corresponding to the final image frame.

The amount of suppression of the signal display can also be varied in some systematic way based on the relationship between the coherently summed signal and incoherently summed signal. For instance, the strength of the signal displayed can be based on the ratio of the incoherently summed signal to the coherently summed signal, or the inverse of the difference between the incoherently summed signal and the coherently summed signal.

In accordance with an alternative preferred embodiment, two ultrasound beams are fired in separate transmits, each beam having the same transmit characteristics and focused at the same transmit focal zone position. This embodiment is utilized when only one receive signal processing path is available. For the first transmit, the receive beamforming time delays are set so that the amplitude of the receive signal at each point along the line represents a coherent signal. When the second beam is transmitted, produce a completely incoherent summation of the receive signals from the transducer. Preferably, the time delays for the second transmit are set equal to 0, i.e., the receive signals in the respective receive channels are not time-delayed. For the second transmit, the amplitude of the receive signal at each point represents the incoherent signal. The display decision process would again be handled as previously described.

DETAILED DESCRIPTION OF THE PREFERRED EMBODIMENTS

Figure 1:
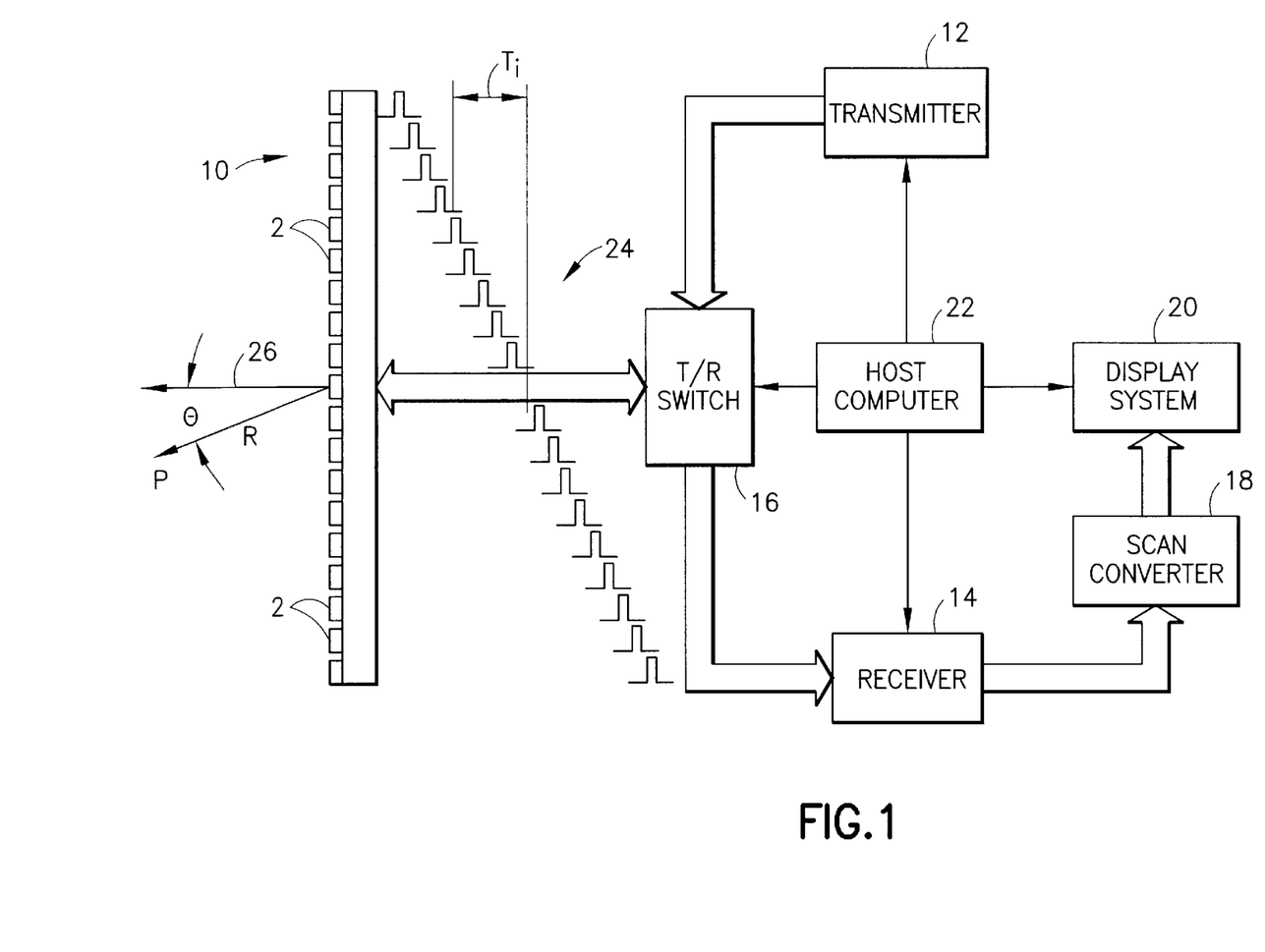
FIG. 1 is a block diagram of an ultrasonic imaging system which incorporates the present invention.

Referring to FIG. 1, a typical ultrasonic imaging system in which the invention can be incorporated comprises a transducer array 10 having a plurality of separately driven transducer elements 2, each of which produces a burst of ultrasonic energy when energized by a pulsed waveform produced by a transmitter 12. The ultrasonic energy reflected back to transducer array 10 from the object under study is converted to an electrical signal by each receiving transducer element 2 and applied separately to a receiver 14 through a set of transmit/receive (T/R) switches 16. Transmitter 12, receiver 14 and T/R switches 16 are operated under control of a host computer (or master controller) 22 responsive to commands by a human operator. A complete scan is performed by acquiring a series of echoes in which switches 16 are set to their transmit position, transmitter 12 is gated ON momentarily to energize each transducer element 2, switches 16 are then set to their receive position, and the subsequent echo signals produced by each transducer element 2 are applied to receiver 14. The separate echo signals from each transducer element 2 are combined in receiver 14 to produce a single echo signal which is used to produce a line in an image on a display system 20.

Transmitter 12 drives transducer array 10 such that the ultrasonic energy produced is directed, or steered, in a focused beam. To accomplish this, transmitter 12 imparts a time delay $T_i$ to the respective pulsed waveforms 24 that are applied to successive transducer elements 2. By adjusting the time delays $T_i$ appropriately in a conventional manner, the ultrasonic beam can be directed away from axis 26 by an angle θ and focused at a fixed range R. A sector scan is performed by progressively changing the time delays $T_i$ in successive excitations. The angle θ is thus changed in increments to steer the transmitted beam in a succession of directions.

Alternatively, in the case of a linear array, a focused beam directed normal to the array is scanned across the object by translating the aperture across the array from one firing to the next. The geometry of a curved array is similar to the linear array geometry except that the elements are set out on a curved surface of constant radius $R_c$. The point reflector is at location (R, θ), but the receiving element is on the arc of the transducer at a radius $R_c$ from the center of curvature. Just as in the case of the linear array, one can figure out the propagation time and the time delay for beams transmitted from a curved array. The present invention is not limited to use with any particular type of transducer array.

Returning to FIG. 1, the echo signals produced by each burst of ultrasonic energy reflect from objects located at successive ranges along the ultrasonic beam. The echo signals are sensed separately by each transducer element 2 and a sample of the magnitude of the echo signal at a particular point in time represents the amount of reflection occurring at a specific range. Due to the differences in the propagation paths between a reflecting point P and each transducer element 2, however, these echo signals will not be detected simultaneously. Receiver 14 amplifies the separate echo signals, imparts the proper time delay to each, and sums them to provide a single echo signal which accurately indicates the total ultrasonic energy reflected from point P located at range R along the ultrasonic beam oriented at the angle θ. The transmit and receive beamforming time delays are provided by the host computer 22.

Scan converter 18 receives the series of acoustic data points produced by receiver 14 and converts the acoustic data into pixel intensity values representing the desired image. In particular, the scan converter converts the acoustic data from polar coordinate (R-θ) sector format or Cartesian coordinate linear format to appropriately scaled Cartesian coordinate display pixel intensity data at the video rate. This scan-converted data is then output for display on a display monitor of a display system 20, which images the time-varying amplitude of the envelope of the signal in accordance with a gray-scale mapping.

The images displayed by the monitor are produced from an image frame of data in which each datum indicates the intensity or brightness of a respective pixel in the display. An image frame may, e.g., comprise a 256×256 data array in which each display pixel intensity datum is an 8-bit binary number that indicates pixel brightness. Each pixel has an intensity value which is a function of the backscatter cross section of a respective sample volume in response to interrogating ultrasonic pulses and the gray-scale mapping employed. The displayed image represents the tissue and/or blood flow in a plane through the body being imaged.

System control is centered in the host computer 22, which accepts operator inputs through the operator interface (e.g., a control panel) and in turn controls the various subsystems. The host computer 22 performs system level control functions. A system control bus (not shown) provides the interface from the host computer to the subsystems. A scan controller (not shown) provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

Figure 2:
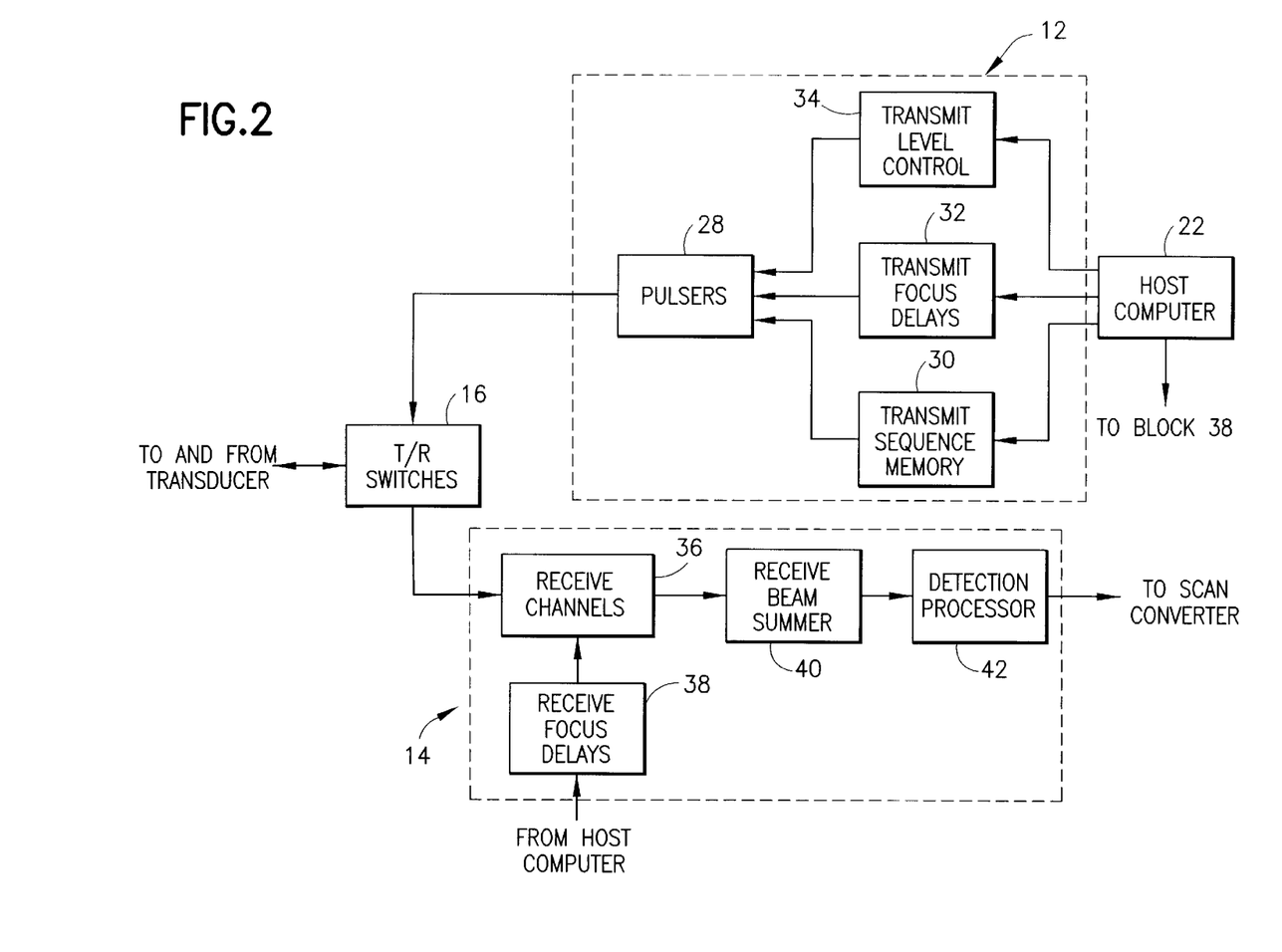
FIG. 2 is a block diagram showing more details of the transmitter and the receiver which form part of the system of FIG. 1.

Transmit beamforming is implemented by programming a digital transmit sequence memory 30 (see FIG. 2). Each transducer element in the transmit aperture is pulsed by a pulse waveform output by a respective pulser 28 in response to a respective transmit sequence output to that pulser from the transmit sequence memory 30. The frequency and length of each pulse waveform is determined by the respective transmit sequence. For example, if the pulser 28 is bipolar, +1 and −1 elements of a transmit sequence are transformed into pulses of opposite phase by pulser, while 0 elements correspond to no pulse. The duty cycle or pulse width is proportional to the number of consecutive +1's or −1's in the transmit sequence.

Under the direction of the host computer 22, the transmitter 12 drives the transducer array such that the ultrasonic energy is transmitted as a directed focused beam. To accomplish focusing, respective time delays are imparted to the pulsers 28 by a transmit focus delay block 32, while respective pulse amplitudes are set by transmit level control block 34. The host computer 22 determines the conditions under which the acoustic pulses will be transmitted. With this information, the transmit focus delay and transmit level control blocks will respectively determine the timing and the amplitude of each of the transmit pulses to be generated by the pulsers 28, while the frequency and length of the transmit pulses are determined by the transmit sequences. In particular, the time delays used by the transmit focus delay block for transmit beamforming originate in the host computer 22. By appropriately adjusting the transmit focus time delays, the ultrasonic beam for each firing can be focused at a desired transmit focal zone position.

After each transmit, the T/R switches 16 are switched to receive mode to pass the returning echoes backscattered from the object being scanned. These return signals are fed to respective receive channels 36 of the receive beamformer. The receive beamformer tracks echoes under the direction of the host computer 22. The receive beamformer imparts the proper receive focus time delays (block 38) to the received RF echo signals. In particular, the time delays used by the receive focus delay block 38 for receive beamforming originate in the host computer. Then the beamsummer 40 sums the RF echo signals from all receive channels to provide an echo signal which accurately indicates the total ultrasonic energy reflected from a succession of ranges corresponding to the particular transmit focal zone.

The beamformer time delays for reception are the same delays ($T_i$) as the transmit beamformer time delays described above. However, the time delay of each receive channel 32 is continuously changing during reception of the echo to provide dynamic focusing of the received beam at the range R from which the echo signal emanates. The receiver 14 tracks the direction θ of the transmit beam steered by transmitter 12, samples the echo signals at a succession of ranges R and employs the proper time delays (or phase shifts) to dynamically focus at points P along the beam, thereby forming a so-called "receive beam". Thus, each transmit of a focused ultrasound beam results in the acquisition of a series of data points which represent the amount of reflected sound from a corresponding series of points P located along the transmit beam.

The receiver further comprises a detection processor 42, which receives the receive beamformer outputs. The detection processor processes the receive signals and then outputs to the scan converter.

Figure 3:
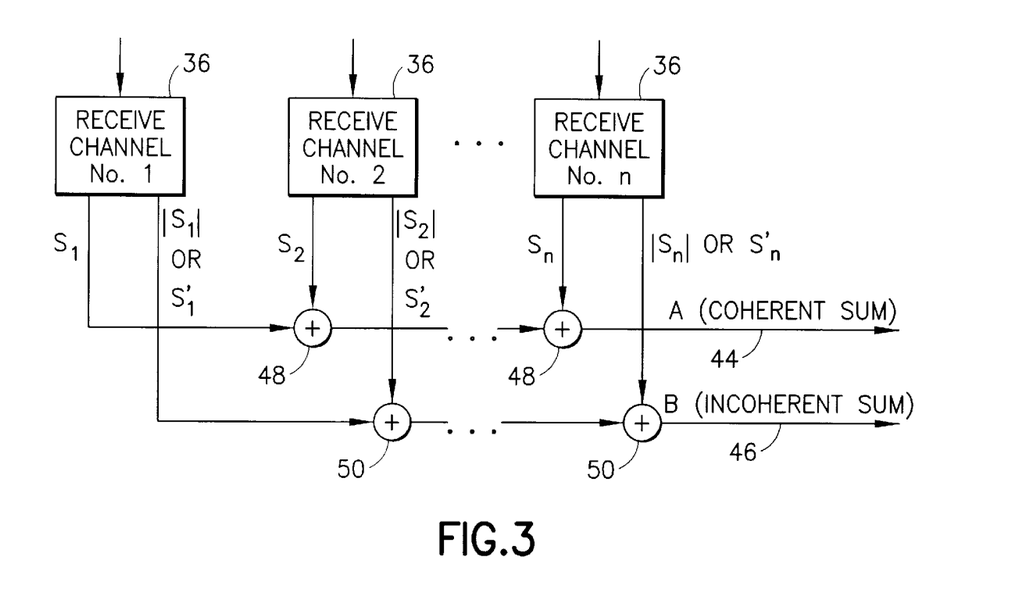
FIG. 3 is a block diagram showing a portion of the receiver in accordance with two alternative preferred embodiments of the invention.

A receive beamformer in accordance with alternative preferred embodiments of the invention is generally depicted in FIG. 3. This receive beamformer comprises a multiplicity of receive channels 36, each receive channel in turn having a pair of parallel receive signal processing paths which carry duplicate receive signals. One receive signal processing path is adapted to produce signed receive samples $s_i$ which are coherent, where i=1, 2, . . . , n, and n is the total number of channels. For this coherent receive signal processing path, this is accomplished by setting the receive beamforming time delays for traditional coherent beamforming. The other receive signal processing path is adapted to produce receive signals which are incoherent. This can be accomplished in at least two different ways. In accordance with the first technique, the receive beamforming time delays are set to force the signed receive samples to be incoherent. For example, time delays may be set equal to zero, i.e., no time delays are used on receive. These signed receive samples are denoted by $s_i'$ in FIG. 3, where again i=1, 2, . . . , n. In accordance with the second technique, the same time delays as those used for coherent beamforming in the other processing path are used in the second receive signal processing path, but the amplitudes, i.e., absolute values, of the time-delayed signed samples, $|S_i|$, i=1, 2, . . . , n, are output, the result being time-delayed unsigned samples.

Regardless of which technique is used to form the incoherent receive samples, the receive samples which are time-delayed using standard coherent beamforming are output to a coherent summation bus 44, which sums the receive samples from each receive channel 36 using pipeline summers 48 to produce a summed signal A. Similarly, the receive samples which are forced to be incoherent are output to an incoherent summation bus 46, which sums the receive samples from each receive channel 36 using pipeline summers 50 to produce a summed signal B. Each of the summed signals A and B consists of a sequence of vectors of data points, one vector for each transmit firing. The summed signals A and B are output to the detection processor 42 (see FIG. 2) for processing in accordance with the preferred embodiments of the invention.

Figure 4:
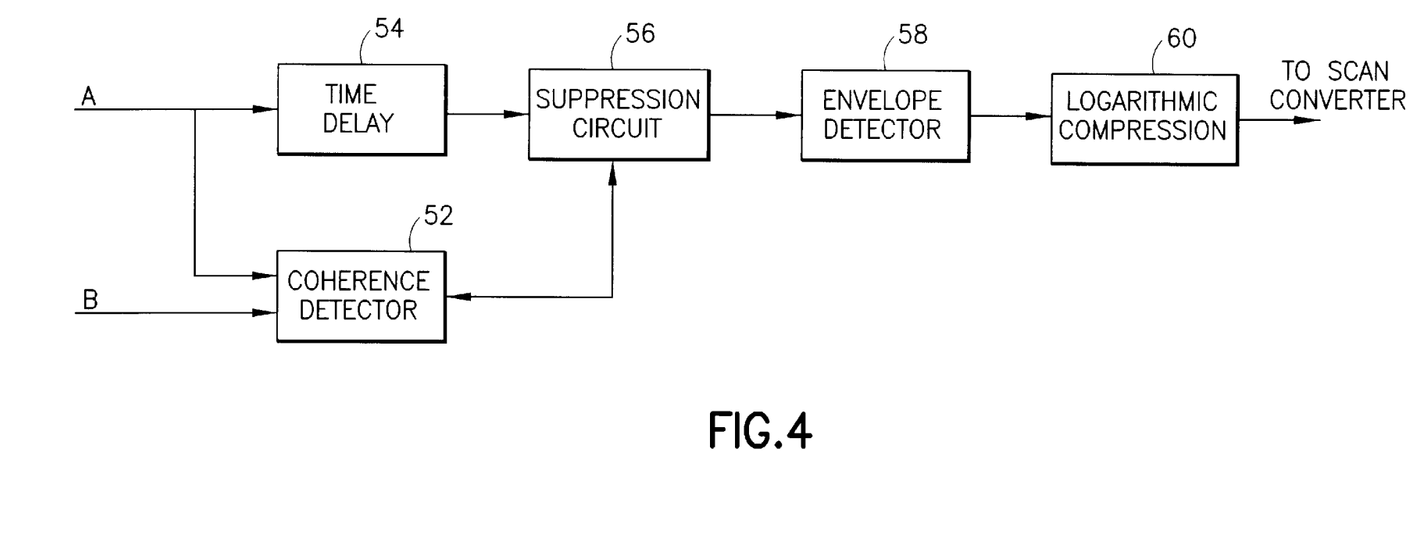
FIG. 4 is a block diagram showing a detection processor in accordance with one preferred embodiment of the invention.

In accordance with one preferred embodiment depicted in FIG. 4, the detection processor comprises a coherence detector 52 having respective inputs for summed signals A and B. The coherence detector 52 is programmed to compare the summed signals A and B and apply a test algorithm which determines the degree of similarity between the two signals and identifies which data points in each vector of summed signal A constitute incoherent data. In particular, if the degree of similarity is greater than a predetermined threshold, the coherence detector 52 decides that the summed signal A, in whole or in part, constitutes incoherent data and outputs a suppression signal for suppressing that incoherent data at some point in the signal processing chain. If the degree of similarity between signals A and B does not meet the predetermined threshold, then the coherence detector 52 does not output the suppression signal. The test algorithm performed by the coherence detector 52 may be altered, e.g., by setting a new predetermined threshold, or replaced by a different test algorithm in accordance with programming received from the host computer.

The control signal is output by the coherence detector 52 to a suppression circuit 56. The latter has an input which receives the summed signal A via a time delay circuit 54. The time delay circuit delays the summed signal A from the receive beamformer by a time interval greater than the processing time required by the coherence detector 52, thereby giving the processor sufficient time in which to determine whether to suppress portions of the summed signal A, e.g., whether to suppress one or more entire vectors or one or more data points within a vector. Preferably the time delay circuit 54 provides a time delay such that the successive data points of the summed signal A are synchronized with the suppression signals, i.e., the incoherent data to be suppressed arrives at the suppression circuit in synchronism with the suppression signal generated in response to detection of that incoherent data by the coherent detector 52. Portions of the summed signal A may be wholly or partially suppressed to produce a coherent summed signal A, which is output to an envelope detector 58. The envelope detector forms the envelope of the coherent summed signal A, which undergoes logarithmic compression (block 60). The logarithmically compressed envelope of the coherent summed signal A is then output to the scan converter for conversion into pixel intensity data.

For the case of a pure time-delay beamformer, the signal in each receive channel is a real, signed quantity. The sum A of the signals si which have been time delayed to form a coherent beam is the arithmetic sum of these real, signed signals. Likewise, the sum B of the signals $s_i'$ which, e.g., have not been time delayed is the arithmetic sum of real, signed signals. Therefore, the coherence detector 52 compares two real signals, A and B.

For the case of a baseband beamformer, the channel signals are complex numbers I+iQ, with real part I and imaginary part Q. The summed signal A is the sum of these complex numbers and is also complex, meaning that the summed signal A has two signal components, a summed in-phase signal $I_A$ and a summed quadrature signal $Q_A$. Likewise, the summed signal B is complex, meaning that the summed signal B has two signal components, a summed in-phase signal $I_B$ and a summed quadrature signal $Q_B$. Therefore, the coherence detector, which compares two complex numbers, receives four inputs from the baseband receive beamformer: $I_A$ $Q_A$, $I_B$ and $Q_B$. After the signals $I_A$ and $Q_A$ are passed through the suppression circuit 56, the envelope detector 58 forms the envelope of the complex signal pair by computing $(I_A^2+Q_A^2)^{1/2}$.

Figure 5:
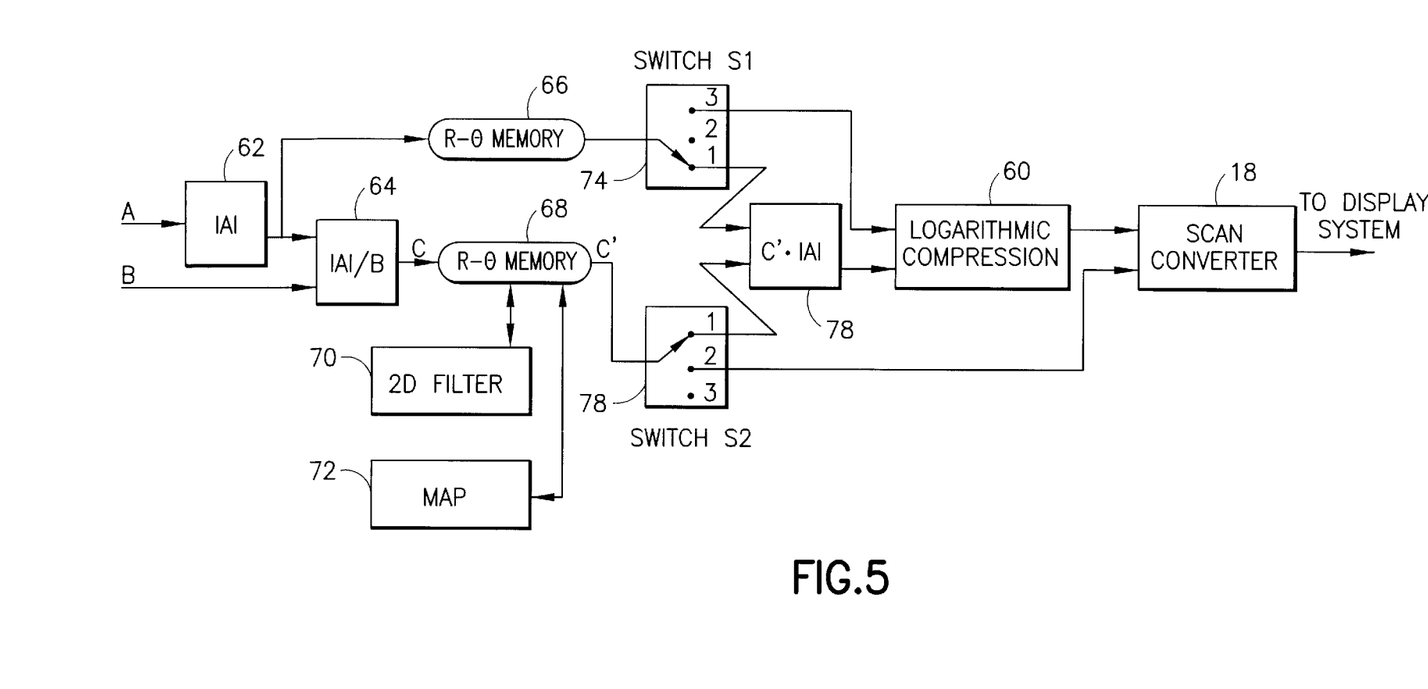
FIG. 5 is a block diagram showing a detection processor in accordance with another preferred embodiment of the invention.

FIG. 5 shows another preferred embodiment of the detection processor 52 (shown in FIG. 2), which is used in conjunction with the version of the receive beamformer in which $s_i$ and $|s_i|$ are output in parallel from each channel. In this embodiment the detection processor calculates and applies a coherence factor C. The coherence factor is calculated for each data point in the receive signal, i.e., for each pixel in the image. The coherence factor is defined to be the ratio of two quantities: the amplitude of the sum of the receive signals $s_i$ and the sum of the amplitudes $|s_i|$ of the receive signals:

$$C = \left|\sum_{i=1}^{N} s_i\right| / \sum_{i=1}^{N} |s_i| \tag{1}$$

Referring to FIG. 5, the ratio given in Eq. (1) is calculated in the detection processor by calculating the absolute value of the coherent sum A (block 62) and then calculating the ratio of the absolute value of the coherent sum A to the incoherent sum B (block 64), i.e., C=|A|/B.

For the case of a pure time-delay beamformer, the sum B of the absolute values of the time-delayed signals $s_i$ is the sum of real, unsigned signals, i.e., non-negative numbers. As previously noted, the sum A is the arithmetic sum of real, signed signals.

For the case of a baseband beamformer, summed signal A is the sum of complex numbers and is also complex. The absolute value of this complex number is a real, non-negative number, i.e., $(I^2+Q^2)^{1/2}$. The incoherent sum for the baseband beamformer is the sum of the absolute values of each (complex) channel signal, i.e., a real, non-negative number.

Thus the coherence factor C is a real, non-negative quantity. The minimum value of C is zero, since it is the ratio of two non-negative numbers. The denominator in Eq. (1) can vanish only if all the $s_i$-s are zero. In this case, the numerator also vanishes, the definition C=0 is adopted in this case. The maximum value of C is unity. This follows from Bessel's inequality:

$$|A+B| \leq |A|+|B| \tag{2}$$

where A and B are any two vectors. C equals unity only when $s_i$ is a constant independent of i, that is, when the receive signals are perfectly coherent, i.e., identical, across the transducer array.

It can be advantageous to spatially filter the coherence factor because—like the normal amplitude image—the coherence factor suffers from speckle noise. The coherence information can be spatially filtered to reduce this speckle noise without significantly degrading the apparent resolution of the final image in those cases (transparent overlay and modified gray scale) in which the coherence data is not displayed independently. For example, the coherence factor can be filtered with a simple 5×5 filter which substitutes the average of the 25 values for the center value in the 5×5 filter kernel. The use of spatial filtering increases the contrast between the bright and dark areas of the kidney, for example, and within fat and muscle layers.

Figure 6:
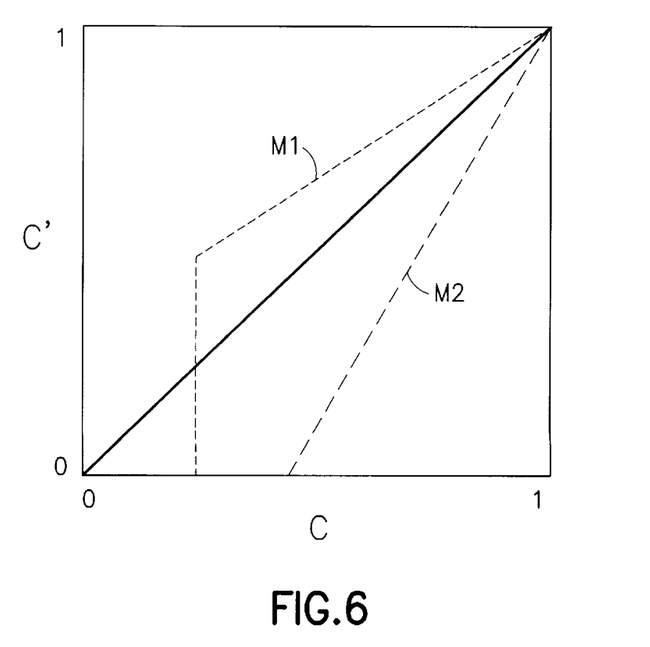
FIG. 6 is a graph showing mappings for the coherence factor C in accordance with the preferred embodiment of FIG. 5. The solid line is the default (no mapping) and the dashed lines show two linear mappings with thresholds.

In accordance with a further optional feature, the coherence factor can be mapped before displaying it or applying it to the amplitude image, in order to optimize the coherence data for particular imaging applications. For example, the alternate mappings M1 and M2 shown in FIG. 6 would zero out the data when the coherence factor C falls below a predetermined threshold. This can be useful in cases where the primary diagnostic concern is identifying blood vessels in an image.

The coherence factor C provides independent information about the tissue. It can be displayed as a separate image or as a transparent color map overlaid on the B-mode image. Alternatively, the coherence information can be combined with the amplitude information and displayed as a single gray-scale image. In the simplest case, this combination consists of multiplying, sample by sample, the receive beamformed amplitude by the coherence factor, and then displaying the modified amplitude conventionally (logarithmic compression and scan conversion).

FIG. 5 depicts a system which can be selectively operated to display the coherence information alone, the amplitude information alone or a combination of the coherence and amplitude information. In accordance with the preferred embodiment of the invention, the amplitude of the coherent sum, i.e., |A|, is placed into a R-θ buffer memory 66 which holds the samples for each range R and for each scan line direction θ. The coherence factor C, calculated as described above, is placed into a separate R-θ buffer memory 68. Optionally, the coherence information is filtered and scaled. The filtering and scaling operations are performed in buffer 68 by applying a two-dimensional filter 70 and a coherence map 72. The filtered and scaled coherence factor data is indicated by output C' in FIG. 5.

The output |A| of memory 66 is coupled to the input of a three-position switch 74. When switch 74 is set to position 1, the input to switch 74 is output to a first input of a multiplier 78. When switch 74 is set to position 2, the input to switch 74 is not used. When switch 74 is set to position 3, the input to switch 74 is output to a memory 60 which stores logarithmic compression look-up tables.

Similarly, the output C' of memory 68 is coupled to the input of a three-position switch 76. When switch 76 is set to position 1, the input to switch 76 is output to a second input of multiplier 78. When switch 76 is set to position 2, the input to switch 76 is output to scan converter 20. When switch 76 is set to position 3, the input to switch 76 is not used.

In accordance with a first operating mode, only the coherence data is displayed. This is accomplished by setting both of switches 74 and 76 to position 2. In this state, the output C' is sent directly to the scan converter 20. The scan-converted coherence data is then displayed on a linear scale by the display system (20 in FIG. 1).

In accordance with a second operating mode, only the amplitude data is displayed. This is accomplished by setting both of switches 74 and 76 to position 3. In this state, the output |A| is sent directly to the logarithmic compression memory 72. The amplitude data is logarithmically compressed in memory 72 and then scan-converted by scan converter 20 in a conventional manner. The log-compressed, scan-converted amplitude data is then displayed by the display system.

In accordance with a third operating mode, the product of the coherence and amplitude data is displayed. This is accomplished by setting both of switches 74 and 76 to position 1. In this state, the outputs |A| and C' are sent to respective inputs of multiplier 78. The multiplier 78 multiplies, sample by sample, the amplitude data by the respective coherence factors. The modified amplitude data is then log-compressed, scan-converted and displayed in a conventional manner.

The foregoing preferred embodiments have been disclosed for the purpose of illustration. Variations and modifications which do not depart from the broad concept of the invention will be readily apparent to those skilled in the pertinent art. For example, although a preferred embodiment has been disclosed in which the suppression circuit is placed before the envelope detector, the incoherent data points can be suppressed at any stage in the signal processing chain between the receive beamformer output and the display monitor. In particular, suppression may be performed in the envelope detector, in the scan converter or in a video processor situated between the scan converter and the display monitor. In addition, the suppression operation includes either reducing the amplitude of acoustic data to be imaged in response to a suppression signal from the coherence detector or nulling acoustic data to be imaged in response to that suppression signal. All such variations and modifications are intended to be encompassed by the claims set forth hereinafter.

As used in the claims, the phrase "as a function of" is not to be construed to mean "as a function of only" what follows. For example, in accordance with the foregoing definition, the phrase "determine y as a function of x" would read on all cases where y was determined as a function of x alone or as a function of x and one or more other variables, e.g., z.

We claim:

1. An imaging system comprising:
    a transducer array comprising a multiplicity of transducer elements;
    a transmit beamformer for pulsing said transducer array in a transmit mode to transmit a beam of wave energy focused in a transmit focal zone;
    a receive beamformer coupled to said transducer array in a receive mode for forming a first vector of acquired data by summing echo signals with time delays designed to beamform echoes from said transmit focal zone;
    a incoherent summer coupled to said transducer array in said receive mode for forming a second vector of acquired data by incoherently summing said echo signals;
    a signal processing chain for converting said first vector of acquired data into a vector of imaging data, said signal processing chain comprising a suppression circuit for suppressing acquired data of said first vector in response to a control signal;
    a coherence processor programmed to output said control signal to said suppression circuit if at least a predetermined degree of similarity exists between said first and second vectors of acquired data; and
    a display device for displaying an image having an image line representing said vector of imaging data.

2. The system as recited in claim 1, wherein said signal processing chain comprises an envelope detector, and said suppression circuit is located upstream of said envelope detector.

3. The system as recited in claim 1, wherein said coherence processor is programmed to determine if at least said predetermined degree of similarity exists by comparing corresponding data points of said first and second vectors to each other, said comparing step being performed along a length of said vectors.

4. The system as recited in claim 1, wherein said suppression circuit reduces the amplitude of acquired data in said first vector in response to said control signal.

5. The system as recited in claim 1, wherein said suppression circuit nulls acquired data in said first vector in response to said control signal.

6. The system as recited in claim 1, wherein said wave energy is ultrasound and said acquired data is acoustic data.

7. The system as recited in claim 1, wherein said receive beamformer and said incoherent summer comprise a multiplicity of receive channels in common.

8. The system as recited in claim 1, wherein said incoherent summer comprises means for summing the magnitudes of said echo signals with said time delays.

9. The system as recited in claim 1, wherein said incoherent summer comprises means for summing said echo signals without time delays.

10. The system as recited in claim 1, wherein said incoherent summer comprises means for summing said echo signals with time delays designed to not beamform echoes from said transmit focal zone.

11. A method for coherent imaging comprising the steps of:
  (a) transmitting a beam of wave energy focused in a transmit focal zone in a medium;
  (b) detecting echo signals from said medium subsequent to said transmitting step;
  (c) forming a first vector of acquired data derived by summing echo signals with time delays designed to beamform echoes from said transmit focal zone;
  (d) forming a second vector of acquired data by incoherently summing said echo signals;
  (e) determining if at least a predetermined degree of similarity exists between said first and second vectors of acquired data;
  (f) suppressing acquired data of said first vector if at least said predetermined degree of similarity exists;
  (g) converting acquired data of said first vector of acquired data into a vector of imaging data if at least said predetermined degree of similarity does not exist; and
  (h) displaying an image having an image line representing said vector of imaging data.

12. The method as recited in claim 11, wherein said step of determining if at least said predetermined degree of similarity exists comprises the steps of comparing corresponding data points of said first and second vectors to each other, said comparing steps being performed along a length of said vectors.

13. The method as recited in claim 11, wherein said step of suppressing comprises the step of reducing the amplitude of acquired data in said first vector if said degree of similarity is greater than said predetermined threshold.

14. The method as recited in claim 11, wherein said step of suppressing comprises the step of nulling acquired data in said first vector if said degree of similarity is greater than said predetermined threshold.

15. The method as recited in claim 11, wherein said wave energy is ultrasound and said acquired data is acoustic data.

16. The method as recited in claim 11, wherein said second vector of acquired data is formed by summing the magnitudes of said echo signals with said time delays.

17. The method as recited in claim 11, wherein said second vector of acquired data is formed by summing said echo signals without time delays.

18. The method as recited in claim 11, wherein said second vector of acquired data is formed by summing said echo signals with time delays designed to not beamform echoes from said transmit focal zone.

19. An imaging system comprising:
  (a) means for transmitting a beam of wave energy focused in a transmit focal zone in a medium;
  (b) means for detecting echo signals from said medium subsequent to said transmitting step;
  (c) means for forming a first vector of acquired data derived by summing echo signals with time delays designed to beamform echoes from said transmit focal zone;
  (d) means for forming a second vector of acquired data by incoherently summing said echo signals;
  (e) means for determining if at least a predetermined degree of similarity exists between said first and second vectors of acquired data;
  (f) means for suppressing acquired data of said first vector if at least said predetermined degree of similarity exists;
  (g) means for converting acquired data of said first vector of acquired data into a vector of imaging data if at least said predetermined degree of similarity does not exist; and
  (h) means for displaying an image having an image line representing said vector of imaging data.

20. An imaging system comprising:
  a transducer array comprising a multiplicity of transducer elements;
  a display device for displaying an image having an image line representing a vector of imaging data; and
  a computer programmed to perform the following steps:
    (a) driving said transducer elements to transmit a beam of wave energy focused in a transmit focal zone;
    (b) forming a first vector of acquired data derived by summing echo signals detected by said transducer elements with time delays designed to beamform echoes from said transmit focal zone;
    (c) forming a second vector of acquired data by incoherently summing said echo signals;
    (d) determining if at least a predetermined degree of similarity exists between said first and second vectors of acquired data;
    (e) suppressing acquired data of said first vector if at least said predetermined degree of similarity exists;
    (f) converting acquired data of said first vector of acquired data into a vector of imaging data if at least said predetermined degree of similarity does not exist; and
    (g) controlling said display device to display an image having an image line representing said vector of imaging data.

21. The system as recited in claim 20, wherein said wave energy is ultrasound and said acquired data is acoustic data.

22. The system as recited in claim 20, wherein said computer forms said second vector of acquired data by summing the magnitudes of said echo signals with said time delays.

23. The system as recited in claim 20, wherein said computer forms said second vector of acquired data by summing said echo signals without time delays.

24. The system as recited in claim 20, wherein said computer forms said second vector of acquired data by summing said echo signals with time delays designed to not beamform echoes from said transmit focal zone.

25. An imaging system comprising:
  a transducer array comprising a multiplicity of transducer elements;
  a transmit beamformer for pulsing said transducer array in a transmit mode to transmit a beam of wave energy focused in a transmit focal zone;
  a receive beamformer coupled to said transducer array in a receive mode for forming a first vector of acquired data by summing echo signals with time delays designed to beamform echoes from said transmit focal zone;
  an incoherent summer coupled to said transducer array in said receive mode for forming a second vector of acquired data by incoherently summing said echo signals;

a coherence processor for forming a vector of coherence factor data by computing a coherence factor for each corresponding pair of data points of said first and second vectors of acquired data; and a display device for displaying an image having an image line representing said vector of coherence factor data.

26. The system as recited in claim 25, wherein said wave energy is ultrasound and said acquired data is acoustic data.

27. The system as recited in claim 25, wherein said incoherent summer comprises means for summing the magnitudes of said echo signals with said time delays to form an incoherent sum for each data point of said second vector, and said coherence processor comprises means for determining the absolute value of each data point of said first vector of acquired data and means for computing a ratio of said absolute value and said incoherent sum for each corresponding pair of data points of said first and second vectors of acquired data.

28. An imaging system comprising:

a transducer array comprising a multiplicity of transducer elements;

a transmit beamformer for pulsing said transducer array in a transmit mode to transmit a beam of wave energy focused in a transmit focal zone;

a receive beamformer coupled to said transducer array in a receive mode for forming a first vector of acquired data by summing echo signals with time delays designed to beamform echoes from said transmit focal zone;

an incoherent summer coupled to said transducer array in said receive mode for forming a second vector of acquired data by incoherently summing said echo signals;

a processor for forming a vector of amplitude data by determining a magnitude for each data point of said first vector of acquired data, forming a vector of coherence factor data by computing a coherence factor for each corresponding pair of data points of said vector of amplitude data and said second vector of acquired data, and forming a vector of composite data by computing a product for each corresponding pair of data points of said vector of amplitude data and said vector of coherence factor data; and a display device for displaying an image having an image line representing said vector of composite factor data.

29. The system as recited in claim 28, wherein said wave energy is ultrasound and said acquired data is acoustic data.

30. A method of coherent imaging comprising the steps of:

(a) transmitting a beam of wave energy focused in a transmit focal zone in a medium;

(b) detecting echo signals from said medium subsequent to said transmitting step;

(c) forming a first vector of acquired data derived by summing echo signals with time delays designed to beamform echoes from said transmit focal zone;

(d) forming a second vector of acquired data by incoherently summing said echo signals;

(e) forming a vector of coherence factor data by computing a coherence factor for each corresponding pair of data points of said first and second vectors of acquired data; and (f) displaying an image having an image line representing said vector of coherence factor data.

31. A method of coherent imaging comprising the steps of:

(a) transmitting a beam of wave energy focused in a transmit focal zone in a medium;

(b) detecting echo signals from said medium subsequent to said transmitting step;

(c) forming a first vector of acquired data derived by summing echo signals with time delays designed to beamform echoes from said transmit focal zone;

(d) forming a second vector of acquired data by incoherently summing said echo signals;

(e) forming a vector of amplitude data by determining a magnitude for each data point of said first vector of acquired data;

(f) forming a vector of coherence factor data by computing a coherence factor for each corresponding pair of data points of said vector of amplitude data and said second vector of acquired data;

(g) forming a vector of composite data by computing a product for each corresponding pair of data points of said vector of amplitude data and said vector of coherence factor data; and (h) displaying an image having an image line representing said vector of composite factor data.

* * * * *